US010980821B2

(12) United States Patent
Lisanti et al.

(10) Patent No.: US 10,980,821 B2
(45) Date of Patent: Apr. 20, 2021

(54) TRIPHENYLPHOSPHONIUM-DERIVATIVE COMPOUNDS FOR ERADICATING CANCER STEM CELLS

(71) Applicant: LUNELLA BIOTECH, INC., Ottawa (CA)

(72) Inventors: Michael P. Lisanti, Fulton, MD (US); Federica Sotgia, Fulton, MD (US)

(73) Assignee: LUNELLA BIOTECH, INC., Ontario (CA)

( * ) Notice: Subject to any disclaimer, the term of this patent is extended or adjusted under 35 U.S.C. 154(b) by 0 days.

(21) Appl. No.: 16/766,472

(22) PCT Filed: Nov. 21, 2018

(86) PCT No.: PCT/US2018/062174

§ 371 (c)(1),
(2) Date: May 22, 2020

(87) PCT Pub. No.: WO2019/104115

PCT Pub. Date: May 31, 2019

(65) Prior Publication Data

US 2020/0376008 A1 Dec. 3, 2020

Related U.S. Application Data

(60) Provisional application No. 62/590,432, filed on Nov. 24, 2017.

(51) Int. Cl.

| | |
|---|---|
| ***A61K 31/66*** | (2006.01) |
| ***A61P 35/00*** | (2006.01) |
| *A61K 45/06* | (2006.01) |

(52) U.S. Cl.

CPC .............. *A61K 31/66* (2013.01); *A61K 45/06* (2013.01)

(58) Field of Classification Search

CPC ................................ A61K 31/66; A61P 35/00
USPC ......................................................... 514/134
See application file for complete search history.

(56) References Cited

U.S. PATENT DOCUMENTS

| | | |
|---|---|---|
| 2010/0105794 A1 | 4/2010 | Dietliker et al. |
| 2014/0228290 A1 | 8/2014 | Spitz et al. |
| 2016/0075726 A1 | 3/2016 | Neuzil |

FOREIGN PATENT DOCUMENTS

| | | |
|---|---|---|
| EP | 3 124 027 | 2/2017 |
| WO | WO 2008/145116 | 12/2008 |
| WO | 2014/124384 | 8/2014 |
| WO | 2016/155679 | 10/2016 |

OTHER PUBLICATIONS

International Search Report for PCT/US2018/062174 dated Mar. 22, 2019, one (1) page.

Written Opinion of the ISA for PCT/US2018/062174 dated Mar. 22, 2019, 14 pages.

Peredo-Silva et al., "Derivatives of alkyl gallate triphenylphosphonium exhibit antitumor activity in a syngenic murine model of mammary adenocarcinoma", Toxicology and Applied Pharmacology, vol. 329, Jun. 21, 2017, pp. 334-336.

Foroodi et al., "Interactions of doxycycline with chemotherapeutic agents in human breast adenocarcinoma MDA-MB-231 cells", Anticancer Drugs., vol. 20, issue 2, Feb. 2009, pp. 115-122.

Severin et al., "Penetrating cation/fatty acid anion pair as a mitochondria-targeted protonophore", PNAS, vol. 107, No. 2, Jan. 12, 2010, pp. 663-668.

Zielonka et al., "Mitochondria-Targeted Triphenylphosphonium-Based Compounds: Syntheses, Mechanisms of Action, and Therapeutic and Diagnostic Applications", Americal Chemical Society, Chem. Rev. 2017, 117, pp. 10043-10120.

India Office Action for India Application No. 202017026372 dated Jan. 25, 2021.

Hosek et al., "Effect of 2-Chloro-Substitution of Adenine Moiety in Mixed-Ligand Gold (I) Triphenylphosphine Complexes on anti-Inflammatory Activity: The Discrepancy Between the In Vivo and the In Vitro Models", PLOS One, www.plosone.org, vol. 1, Issue 11, Nov. 2013, pp. 1-13.

El Salvador Office Action for El Salvador Application No. 2020006065 dated Jan. 12, 2021.

Jara Sandoval, J.A.: "Sintesis de Cationes Trifenilfosfonio Derivados de Estres de Acido Galico y Estudio de su Actividad Citotoxica", Universidad de Chile, Facultad de Ciencias Quimicas y Farmaceuticas, Tesis Doctoral, 2012, 101 paginas.

*Primary Examiner* — Raymond J Henley, III

(74) *Attorney, Agent, or Firm* — Nixon & Vanderhye, P.C.

(57) ABSTRACT

Tri-phenyl-phosphonium (TPP) is a non-toxic chemical moiety that functionally behaves as a mitochondrial targeting signaling in living cells. TPP-related compounds may be utilized to target mitochondria in cancer stem cells (CSCs), and may be used for treating and/or preventing tumor recurrence, metastasis, drug resistance, and/or radiotherapy resistance, as well as for anti-cancer therapies. Various TPP-related compounds validated for oxygen consumption inhibition (OCR), were non-toxic, and had little or no effect on ATP production in normal human fibroblasts. Yet these compounds selectively target adherent "bulk" cancer cells. These compounds also inhibit the propagation of CSCs in suspension. TPP-related compounds provide a novel chemical strategy for effectively targeting both i) "bulk" cancer cells and ii) CSCs, while specifically minimizing or avoiding off-target side-effects in normal cells, among other useful therapies.

27 Claims, 14 Drawing Sheets

7.

8.

9.

Bis-Triphenyl-Phosphonium
(Bis-TPP) Derivatives 2-butene-1,4-bis-TPP p-xylylene-bis-TPP

TRIPHENYLPHOSPHONIUM-DERIVATIVE COMPOUNDS FOR ERADICATING CANCER STEM CELLS

This application is the U.S. national phase of International Application No. PCT/US2018/062174 filed Nov. 21, 2018 which designated the U.S. and claims the benefit of U.S. Provisional Application No. 62/590,432 filed Nov. 24, 2017, the entire contents of each of which are hereby incorporated by reference.

FIELD

This disclosure relates to compounds and therapies for effectively targeting "bulk" cancer cells and cancer stem cells, while minimizing off-target side-effects in normal cells, and more particularly to tri-phenyl-phosphonium (TPP) derivative compounds, or TPP-derivatives, that potently target bulk cancer cells, cancer stem cells, and normal senescent cells, for delivery of therapeutic agents.

BACKGROUND

Conventional cancer therapies, such as irradiation, alkylating agents, and anti-metabolites, work by selectively eradicating fast-growing cancer cells through interfering with cell growth and DNA replication mechanisms. Tumors often recur after such therapies, indicating that not all cancer cells were eradicated. Cancer stem cells (CSCs) are tumor-initiating cells (TICs) that appear to be the biological basis of treatment failure, tumor recurrence and distant metastasis, ultimately leading to poor clinical outcome in cancer patients. As a consequence, new therapies are urgently needed, to specifically target and eradicate CSCs.

Interestingly, recent studies indicate that one unique feature of CSCs is a characteristic increase in mitochondrial mass, which may reflect a more strict dependence on mitochondrial function or OXPHOS. Several independent lines of evidence support the idea that increased mitochondrial biogenesis or higher levels of mitochondrial protein translation may occur in CSCs. For example, unbiased proteomics analysis directly shows that mitochondrial mass is elevated in CSCs.

Moreover, MitoTracker (a mitochondrial fluorescent dye) can be used successfully as a marker to identify and purify CSCs. More specifically, the "Mito-high" cell population shows the greatest capacity for i) anchorage-independent growth and ii) tumor-initiating ability in vivo.

High telomerase activity also directly correlates with high mitochondrial mass and the ability of CSCs to undergo proliferative expansion. Similarly, high mitochondrial mass in CSCs was also specifically associated with mitochondrial reactive oxidative species (ROS) production (hydrogen peroxide) and could be targeted with either: i) mitochondrial anti-oxidants, ii) inhibitors of mitochondrial biogenesis (doxycycline) or OXPHOS, and even iii) inhibitors of cell proliferation (palbociclib, a CDK4/6 inhibitor).

There exists a need in the art for novel and effective anti-cancer therapies, including the development of not only new anti-cancer compounds, but also methods for identifying new classes of compounds having anti-cancer efficacy. Ideal compounds are selective towards cancer cells, including TICs, yet non-toxic to normal cells. This also includes compounds and moieties that specifically target bulk cancer cells, cancer stem cells, and normal senescent cells, for targeted delivery of therapeutic agents.

SUMMARY

This disclosure describes a new approach for the eradication of CSCs and related therapies, through the use of novel mitochondrial inhibitors. Disclosed herein are new strategies for identifying novel and non-toxic mitochondrial targeting signals, including the identity of specific compounds that may be used to enhance the anti-mitochondrial effects of other therapeutic agents. Disclosed herein are also demonstrative embodiments of TPP-conjugate compounds.

Tri-phenyl-phosphonium (TPP) serves as a chemical mitochondrial targeting signal, and also represents a new avenue for safe and effective anti-cancer therapies. Described herein are TPP-derivative compounds that have been developed having a strong preference for uptake in cancer cells (e.g., bulk cancer cells, cancer stem cells, and energetic cancer stem cells), as well as normal but senescent cells. Importantly, TPP-derivatives described herein are non-toxic in healthy cells and normal fibroblasts, but potently target CSC propagation, with an IC-50 as low as 500 nM. As disclosed herein, TPP-derivative 2-butene-1,4-bis-TPP is an example of an effective TPP compound for targeting CSC propagation, among other potential therapies.

The present approach may be used to treat and/or prevent tumor recurrence, metastasis, drug resistance, and/or radiotherapy resistance. Anti-cancer treatments often fail because the tumor recurs or metastasizes, particularly after surgery. Also, drug resistance and radiotherapy resistance are common reasons for cancer treatment failure. It is believed that CSC mitochondrial activity may be, at least in part, responsible for these causes of treatment failure. Embodiments of the present approach may be used in situations where conventional cancer therapies fail, and/or in conjunction with anti-cancer treatments to prevent failure due to tumor recurrence, metastasis, drug resistance, and/or radiotherapy resistance. The present approach may also take the form of a method for targeting a therapeutic agent to a cancer stem cell mitochondria, by chemically modifying the therapeutic agent with at least one TPP-derivative compound.

As used herein, a TPP-derivative is a chemical compound derived from TPP. For example, a TPP-derivative compound may be 2-butene-1,4-bis-TPP; derivatives of 2-butene-1,4-bis-TPP; 2-chlorobenzyl-TPP; derivatives of 2-chlorobenzyl-TPP; 3-methylbenzyl-TPP; derivatives of 3-methylbenzyl-TPP; 2,4-dichlorobenzyl-TPP; derivatives of 2,4-dichlorobenzyl-TPP; 1-naphthylmethyl-TPP; derivatives of 1-naphthylmethyl-TPP; p-xylylenebis-TPP; and derivatives of p-xylylenebis-TPP. It should be appreciated that the foregoing list is not an exhaustive list of TPP-derivatives. As will be appreciated, however, the conjugated moiety(ies) can have a significant impact on whether the TPP-derivative has anti-cancer or other beneficial properties, as well as the potency of those properties.

The present approach may take the form of a method for treating cancer, in which a pharmaceutically effective amount of at least one TPP-derivative compound is administered. The present approach may also take the form of methods and pharmaceutical compositions for treating and/or preventing tumor recurrence, metastasis, drug resistance, and/or radiotherapy resistance, in which a pharmaceutically effective amount of at least one TPP-derivative compound is administered, either in conjunction with or after cancer therapy. The TPP-derivative compound may be administered with a mitochondrial inhibitor or other therapeutic agent, thereby increasing the agent's uptake in cancer cells with little or no effect on normal, healthy cells. The TPP-derivative compound may be 2-butene-1,4-bis-TPP; 2-chlorobenzyl-TPP; 3-methylbenzyl-TPP; 2,4-dichlorobenzyl-TPP; 1-naphthylmethyl-TPP; or p-xylylenebis-TPP. The TPP-derivative compound comprises 2-butene-1,4-bis-TPP in some embodiments. In some embodiments, there may be more than one TPP-derivative. In some embodiments, the TPP-derivative compound is one or more of: derivatives of 2-butene-1,4-bis-TPP; derivatives of 2-chlorobenzyl-TPP; derivatives of 3-methylbenzyl-TPP; derivatives of 2,4-dichlorobenzyl-TPP; derivatives of 1-naphthylmethyl-TPP; and derivatives of p-xylylenebis-TPP.

It should be appreciated that the TPP-derivative compound selectively targets cancer stem cells in embodiments of the present approach. Further, in some embodiments, the at least one TPP-derivative compound selectively targets normal senescent cells. TPP-derivative compounds may be minimally toxic or, in some embodiments, non-toxic, to normal healthy cells.

The present approach may take the form of a composition having, as an active ingredient, at least one TPP-derivative compound. For example, the pharmaceutical composition may be an anti-cancer pharmaceutical composition having, as its active ingredient, at least one TPP-derivative compound. The TPP-derivative compound comprises at least one of: 2-butene-1,4-bis-TPP; derivatives of 2-butene-1,4-bis-TPP; 2-chlorobenzyl-TPP; derivatives of 2-chlorobenzyl-TPP; 3-methylbenzyl-TPP; derivatives of 3-methylbenzyl-TPP; 2,4-dichlorobenzyl-TPP; derivatives of 2,4-dichlorobenzyl-TPP; 1-naphthylmethyl-TPP; derivatives of 1-naphthylmethyl-TPP; p-xylylenebis-TPP; and derivatives of p-xylylenebis-TPP. In some embodiments, for example, the active ingredient is 2-butene-1,4-bis-TPP.

Embodiments of the pharmaceutical composition may eradicate bulk cancer cells, cancer stem cells, and normal senescent cells. Further, the TPP-derivative compound may in embodiments of the present approach be non-toxic towards normal healthy cells.

TPP-derivatives may also eradicate senescent cells, thereby reducing and/or eliminating various aging-related diseases. The present approach may therefore take the form of a method for treating an affliction through administering a pharmaceutically effective amount of at least one TPP-derivative compound. The TPP-derivative compound may be administered with one or more additional therapeutic agents, such as agents having anti-mitochondrial effects. The affliction may be, for example, cancer, an age-associated illness, senescence-associated secretory phenotype, or the effects of aging, such as atherosclerosis, cardiovascular disease, cancer, arthritis, cataracts, osteoporosis, type 2 diabetes, obesity, metabolic syndrome, hypertension, Alzheimer's disease, chronic inflammation, neuro-degeneration, muscle-wasting (sarcopenia), loss of skin elasticity, greying of the hair, male-pattern baldness, age spots, skin imperfections, and keratosis.

BRIEF DESCRIPTION OF THE DRAWINGS

FIG. 1(A) shows: 1. 2-butene-1,4-bis-TPP; 2. 2-chlorobenzyl-TPP; 3. 3-methylbenzyl-TPP; FIG. 1(B) shows: 4. 2,4-dichlorobenzyl-TPP; 5. 1-naphthylmethyl-TPP; 6. mito-TEMPO; and FIG. 1(C) shows: 7. cyanomethyl-TPP; 8. p-xylylene-bis-TPP; and 9. 4-cyanobenzyl-TPP.

DESCRIPTION

The following description illustrates embodiments of the present approach in sufficient detail to enable practice of the present approach. Although the present approach is described with reference to these specific embodiments, it should be appreciated that the present approach may be embodied in different forms, and this description should not be construed as limiting any appended claims to the specific embodiments set forth herein. Rather, these embodiments are provided so that this disclosure will be thorough and complete, and will fully convey the scope of the present approach to those skilled in the art.

The inventors previously identified the approach of inhibiting mitochondrial function in CSCs and TICs as an avenue for eradicating cancer cells. Given the role of mitochondrial biogenesis in tumor proliferation, the inventors recognized that mitochondrial targeting represents a valuable characteristic for anti-cancer therapies. Tri-phenyl-phosphonium (TPP) is a well-established chemical mitochondrial targeting signal. Cargo molecules covalently attached to TPP accumulate within the mitochondria of living cells. However, successful anti-cancer therapies require targeting cancer cells, as opposed to normal cells. As discussed herein, certain TPP-derivatives have been developed that not only selectively target cancer cell mitochondria, but also have minimal-to-no side-effects in normal cells.

In order to identify new molecules that can be used to target mitochondria within CSCs, the inventors screened a variety of TPP-derivatives as described herein, by employing CellTiter-Glo to measure intracellular levels of ATP in adherent cancer cells (MCF-7) in 96-well plates. As 85% of cellular ATP is normally derived from mitochondrial metabolism, ATP levels are an excellent read-out to monitor mitochondrial function. In parallel, the same 96-well plates were also stained with Hoechst 33342, to measure DNA content, to gauge cell viability. Therefore, we randomly selected 9 TPP derivatives and subjected them to screening in our assay system. The chemical structures of these TPP-derivatives are shown in FIG. 1.

TPP, as a mitochondrial targeting signaling, is non-toxic in normal cells. The inventors recognized that TPP-derivative compounds could be developed to inhibit mitochondrial function in CSCs, and developed the approach shown in FIG. 10 for identifying such compounds. To demonstrate this approach, the inventors used an ATP depletion assay to screen the activity of the nine TPP-derivatives shown in FIG. 1, which include: (1) 2-butene-1,4-bis-TPP; (2) 2-chlorobenzyl-TPP; (3) 3-methylbenzyl-TPP; (4) 2,4-dichlorobenzyl-TPP; (5) 1-naphthylmethyl-TPP; (6) mito-TEMPO (synonymous with (2-(2,2,6,6-Tetramethylpiperidin-1-oxyl-4-ylamino)-2-oxoethyl)triphenylphosphonium chloride); (7) cyanomethyl-TPP; (8) p-xylylene-bis-TPP; and (9) 4-cyanobenzyl-TPP.

Figure 11:
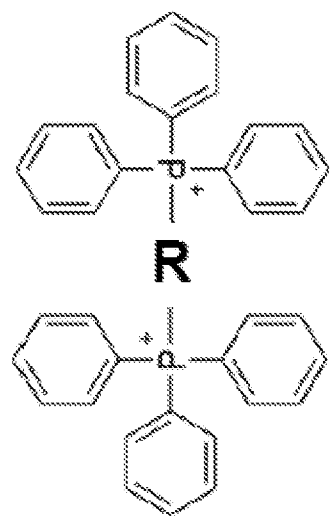
FIG. 11 illustrates a TPP Compound also referred to as bis-TPP.

Five of the screened TPP-related compounds significantly suppressed ATP levels, which yields a hit-rate of more than 50%. All five positive hit compounds were subjected to functional validation with the Seahorse XFe96, to quantitate their effects on the mitochondrial oxygen consumption rate (OCR). Remarkably, these TPP hit compounds were non-toxic in normal human fibroblasts and did not affect their viability or ATP production, showing striking selectivity for cancer cells. Most importantly, these top hit compounds successfully blocked CSC propagation, as shown by employing the 3D spheroid assay. For example, 2-butene-1,4-bis-TPP was that most potent molecule that we identified, which targeted CSC propagation with an IC-50<500 nM. Interestingly, 2-butene-1,4-bis-TPP contains two TPP groups. This suggests that the use of a bis-TPP moiety, such as shown in FIG. 11, may function as a “dimeric” or “polymeric” signal for the more effective targeting of mitochondria in CSCs. Further studies are contemplated to continue exploring the potential of bis-TPP as a highly effective therapeutic agent.

Notably, five out of the nine TPP-derivative compounds were “positive hits” that significantly reduced ATP levels. These positive hits included: 2-butene-1,4-bis-TPP, 2-chlorobenzyl-TPP, 3-methylbenzyl-TPP, 2,4-dichlorobenzyl-TPP and 1-naphthylmethyl-TPP. This represents a hit rate of >50% of the TPP-derivatives subject to the demonstrative study. However, two compounds were completely ineffective in reducing ATP levels (see Table 1). This finding is consistent with previous studies showing that the TPP moiety is not intrinsically toxic for normal cell mitochondria.

After initial screening, the five positive hit compounds were then subjected to further validation studies, shown in FIGS. 2-4, demonstrating that these TPP compounds are highly active in the range of 0.5 to 2 μM. Based on this initial analysis, 2-butene-1,4-bis-TPP demonstrated the highest potency of the positive hit TPP-derivatives.

Figure 1A:
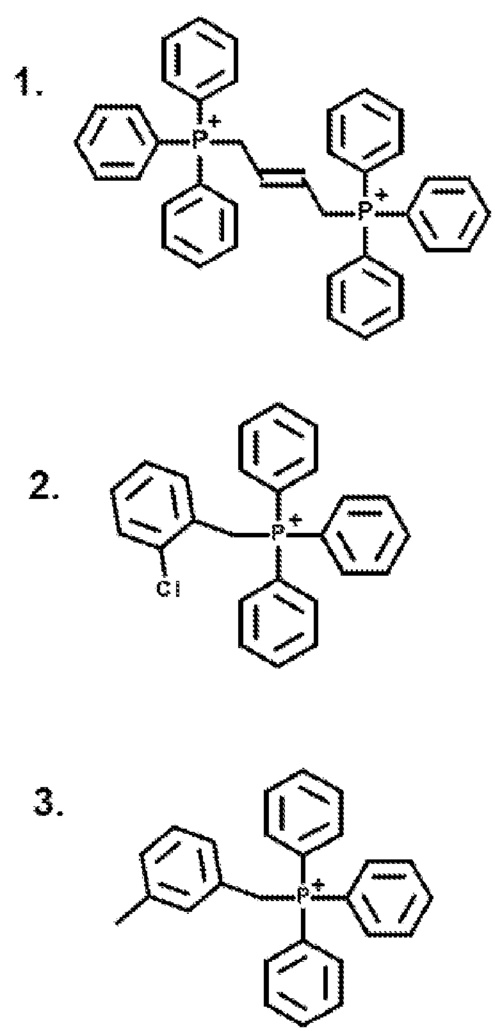
FIGS. 1(A)-1(C) show the structures of nine TPP-derivatives, also referenced as TPP Compounds 1-9.
Figure 1B:
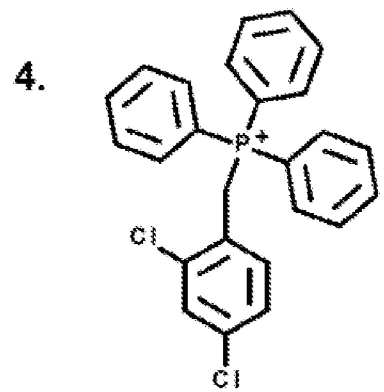
Figure 1B:
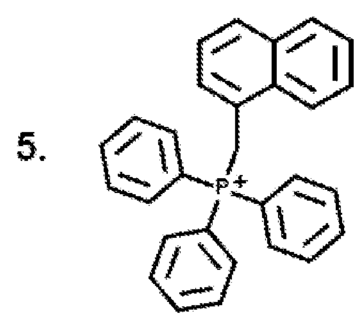
Figure 1B:
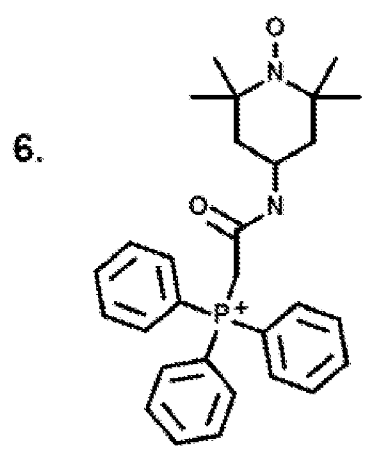
Figure 1C:
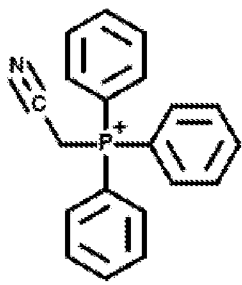
Figure 1C:
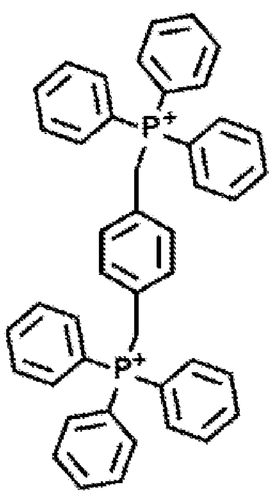
Figure 1C:
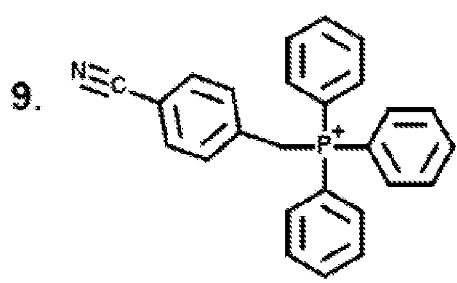
Figure 2A:
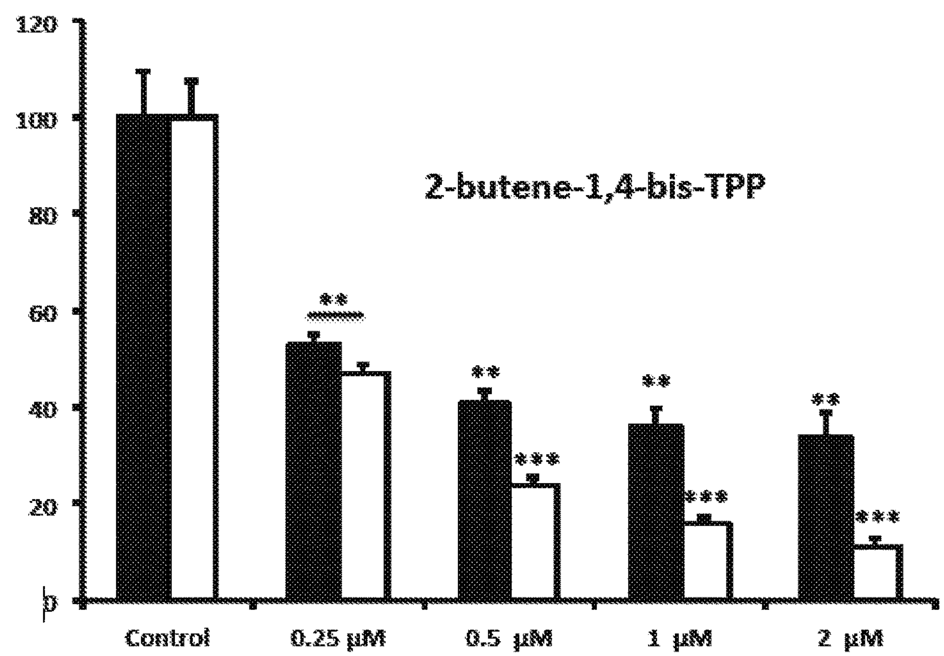
FIGS. 2A and 2B show the effect of TPP-derivatives on cell viability and intracellular ATP levels in MCF-7 human breast cancer cells for TPP Compound 1 (2-butene-1,4-bis-TPP).
Figure 2B:
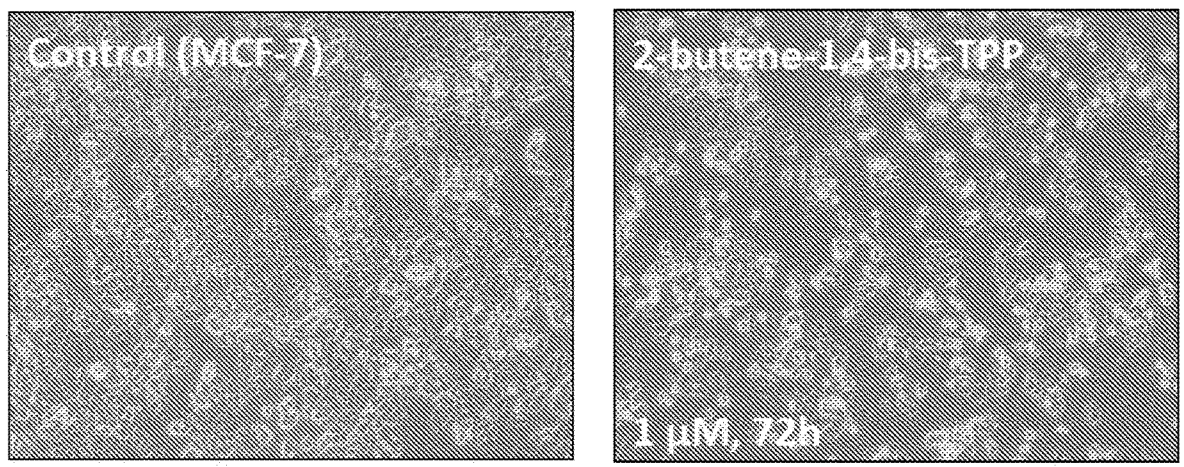

FIG. 2A shows the effect of TPP Compound 1, 2-butene-1,4-bis-TPP, on cell viability and intracellular ATP levels in MCF-7 human breast cancer cells. Cell viability and intracellular ATP levels were determined in the same treated samples. Hoechst staining (%) (shown in black bars); ATP levels (%) indicated in the white bars. MCF-7 cells were treated for 72 h. Data are represented as mean+/−SEM. Note that 2-butene-1,4-bis-TPP depletes ATP levels, relative to cell number. p<0.01; *p<0.001; indicates significance, all relative to the control. FIG. 2B shows a magnified image of control and treated cell plates.

Figure 3A:
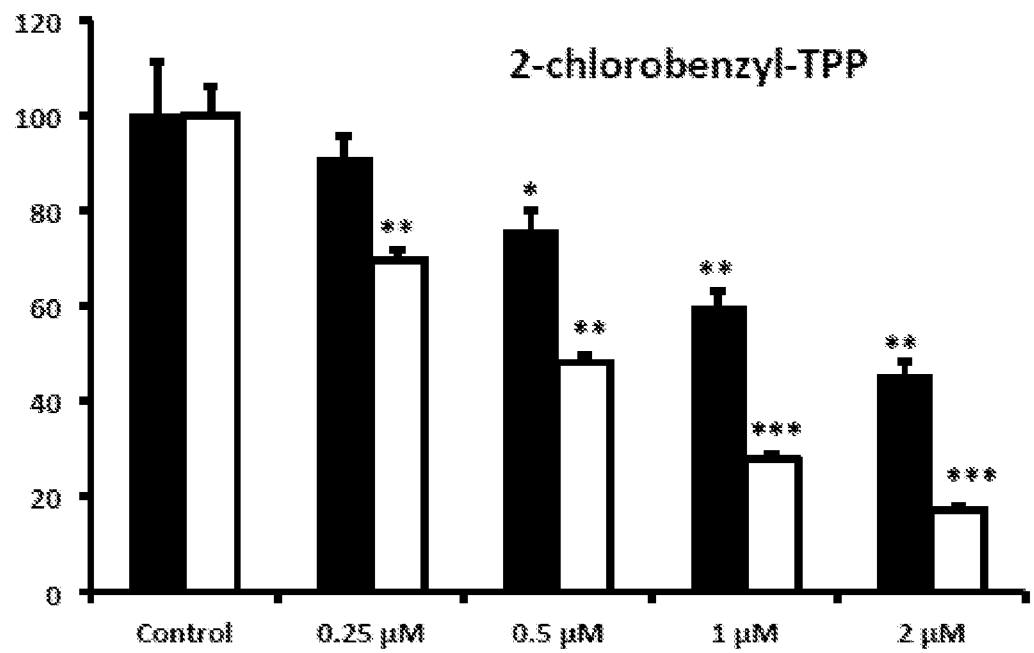
FIGS. 3A and 3B illustrate the e Effect of TPP-derivatives on cell viability and intracellular ATP levels in MCF-7 human breast cancer cells for TPP Compounds 2 (2-chlorobenzyl-TPP) and 3 (3-methylbenzyl-TPP).
Figure 3B:
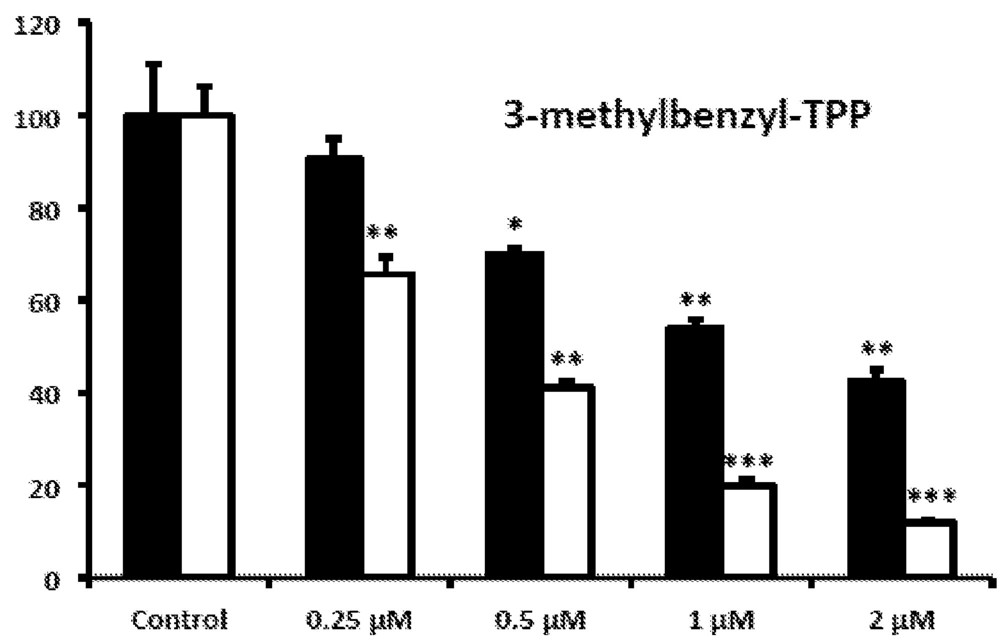

FIGS. 3A and 3B show the effect of TPP Compound 2 (2-chlorobenzyl-TPP) and TPP Compound 3 (3-methylbenzyl-TPP) on cell viability and intracellular ATP levels in MCF-7 human breast cancer cells. Cell viability and intracellular ATP levels were determined in the same treated samples. Hoechst staining (%) (shown in black bars); ATP levels (%) indicated in white bars. MCF-7 cells were treated for 72 h. Data are represented as mean+/−SEM. Note that both 2-chlorobenzyl-TPP and 3-methylbenzyl-TPP progressively deplete cellular ATP levels. *p<0.05; p<0.01; *p<0.001; indicates significance, all relative to the control.

Figure 4A:
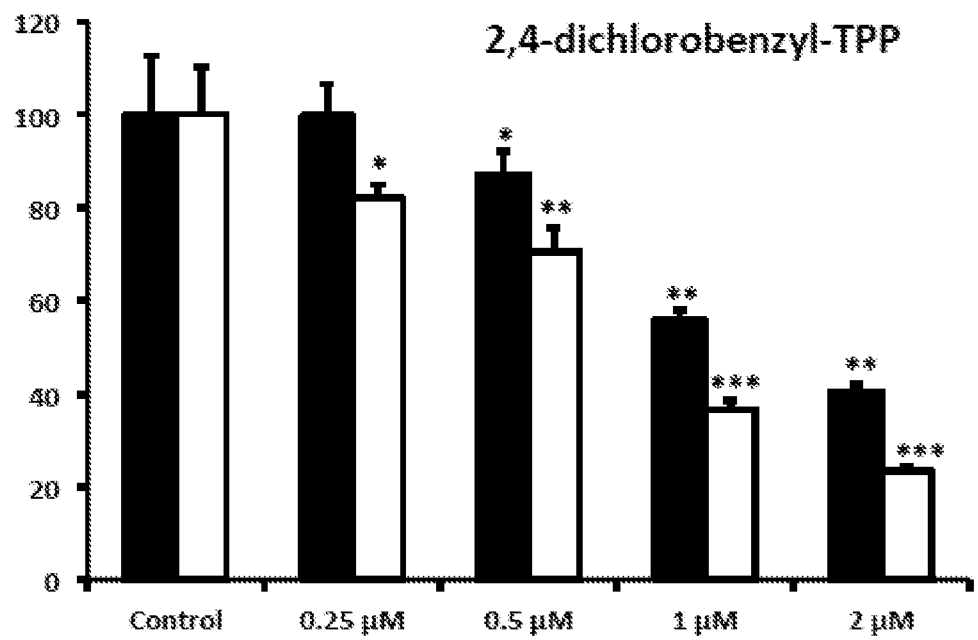
FIGS. 4A and 4B show the effect of TPP-derivatives on cell viability and intracellular ATP levels in MCF-7 human breast cancer cells for TPP Compounds 4 (2,4-dichlorobenzyl-TPP) and 5 (1-naphthylmethyl-TPP).
Figure 4B:
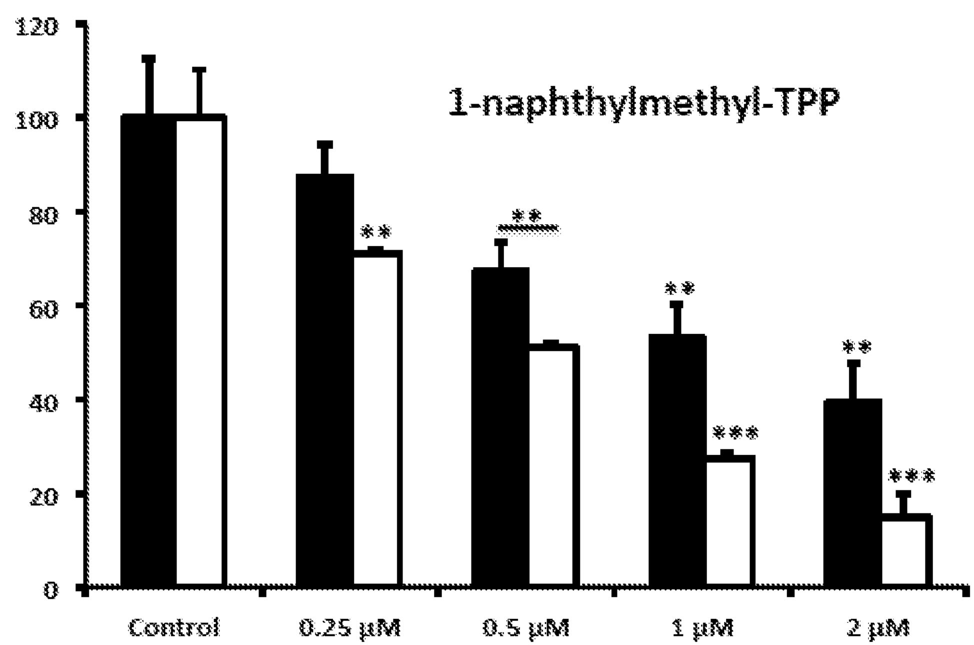

FIGS. 4A and 4B show the effect of TPP Compound 4 (2,4-dichlorobenzyl-TPP) and TPP Compound 5 (1-naphthylmethyl-TPP) on cell viability and intracellular ATP levels in MCF-7 human breast cancer cells. Cell viability and intracellular ATP levels were determined in the same treated samples. Hoechst staining (%) (shown in black bars); ATP levels (%) indicated in white bars. MCF-7 cells were treated for 72 h. Data are represented as mean+/−SEM. Note that both 2,4-dichlorobenzyl-TPP and 1-naphtylmethyl-TPP progressively deplete cellular ATP levels. *p<0.05; p<0.01; *p<0.001; indicates significance, all relative to the control.

Figure 5:
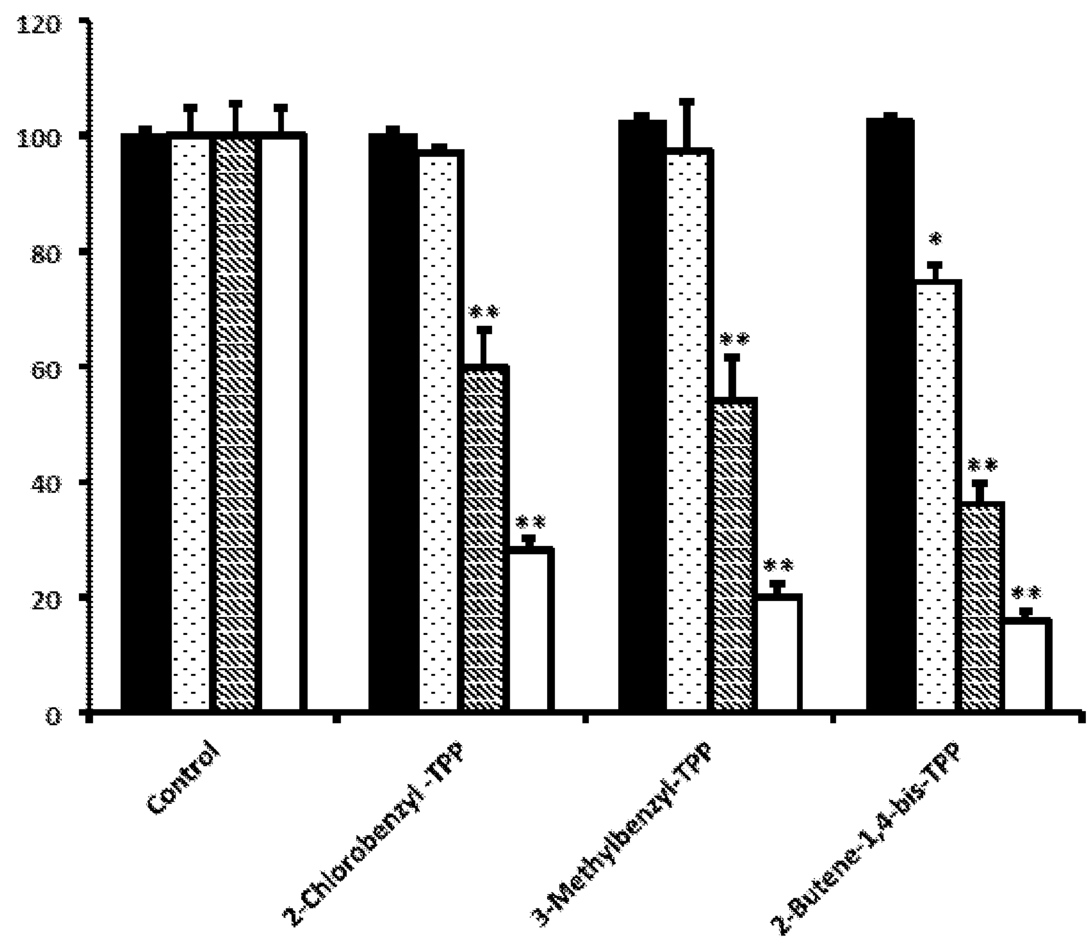
FIG. 5 illustrates the effects of TPP-derivatives on cell viability and intracellular ATP levels in normal fibroblasts (hTERT-BJ1) and human breast cancer cells (MCF-7).

FIG. 5 shows the effects of TPP-derivatives on cell viability and intracellular ATP levels in normal fibroblasts (hTERT-BJ1) and human breast cancer cells (MCF-7). Cell viability and intracellular ATP levels were determined in the same treated samples. Hoechst staining (%) of hTERT-BJ1 human fibroblasts (black); ATP level (%) of hTERT-BJ1 human fibroblasts (dotted); Hoechst staining (%) of MCF-7 cells (inclined lines); ATP level (%) of of MCF-7 cells (white). TPP treatments at 1 μM, 72 h. Data are represented as mean+/−SEM. *p<0.05; **p<0.01; indicates significance, all relative to the control.

As can be seen in FIG. 5, these TPP-derivatives are relatively non-toxic in normal human fibroblasts (hTERT-BJ1), but are preferentially active in cancer cells (MCF-7). For example, in human fibroblasts, 2-butene-1,4-bis-TPP had no effect on cell viability and only mildly reduced ATP levels by 25%. In contrast, at the same concentration (1 μM) in MCF-7 cancer cells, 2-butene-1,4-bis-TPP reduced cell viability by nearly 65% and decreased ATP levels by almost 85%. Therefore, 2-butene-1,4-bis-TPP was 2.8-fold more effective at reducing cell viability in cancer cells (versus fibroblasts). Similarly, 2-butene-1,4-bis-TPP was 4.7-fold more effective at reducing ATP levels in cancer cells, relative to normal fibroblasts.

Figure 6:
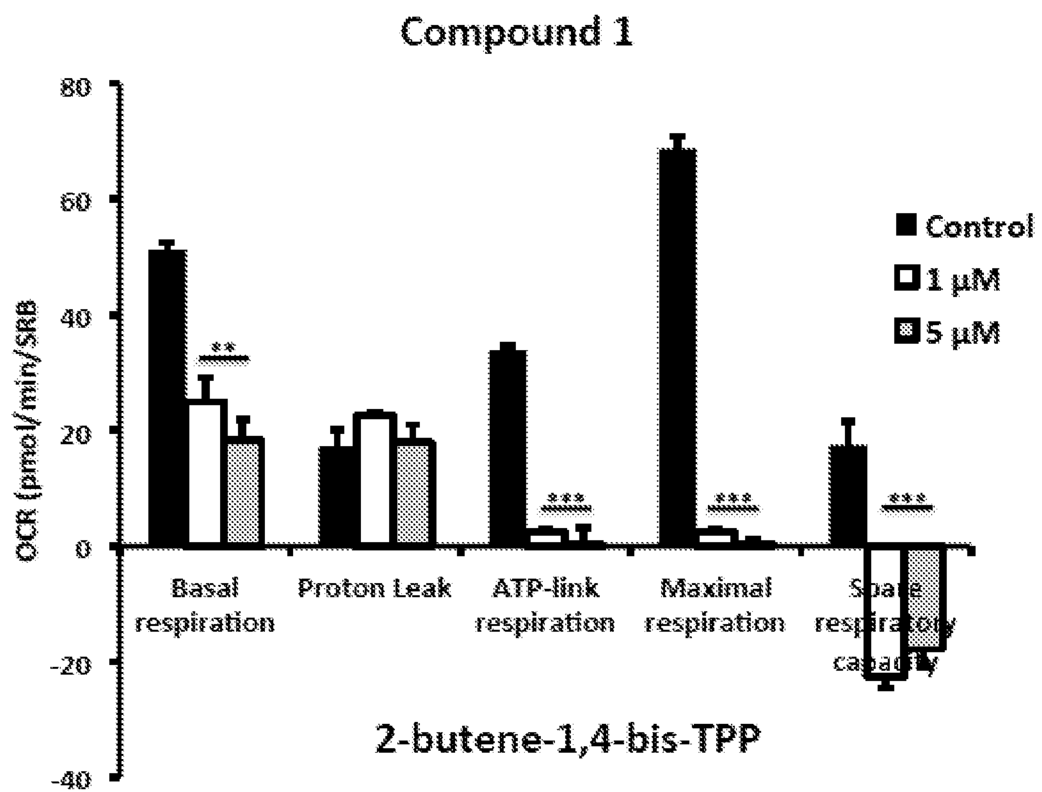
FIG. 6 illustrates impaired mitochondrial function of MCF-7 cells after treatment with TPP Compound 1 (2-butene-1,4-bis-TPP).
Figure 7A:
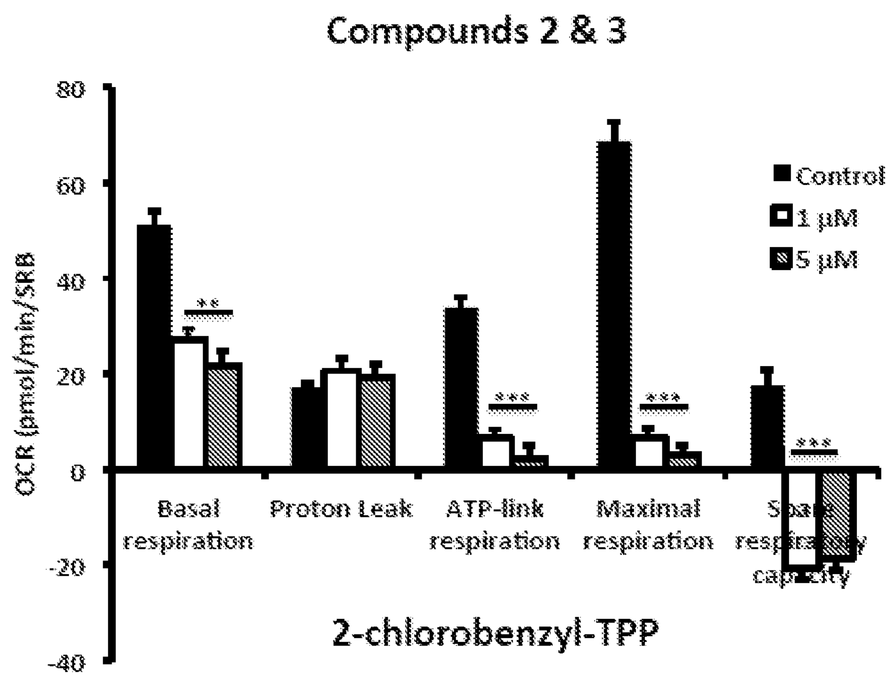
FIGS. 7A and 7B illustrate impaired mitochondrial function of MCF-7 cells after treatment with TPP Compounds 2 (2-chlorobenzyl-TPP) and 3 (3-methylbenzyl-TPP).
Figure 7B:
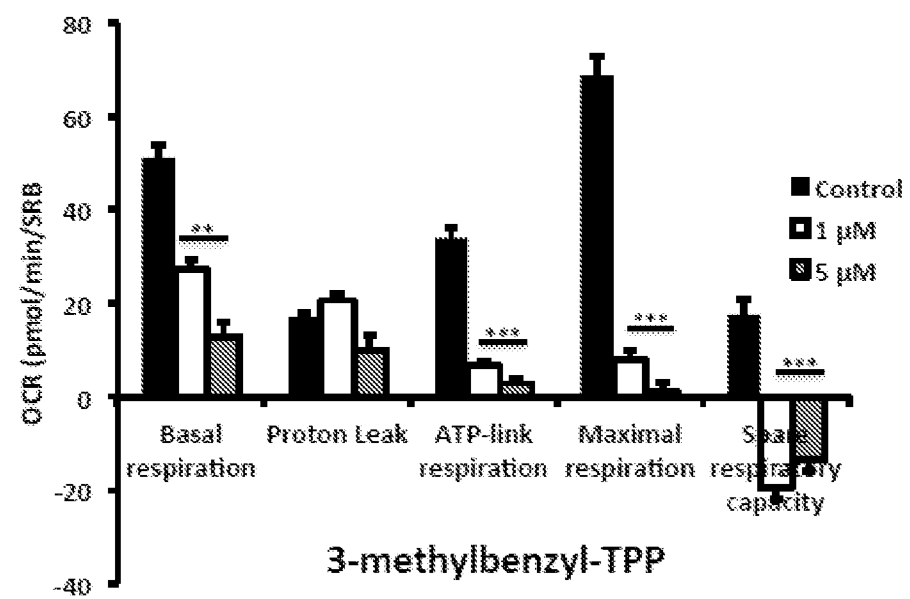
Figure 8A:
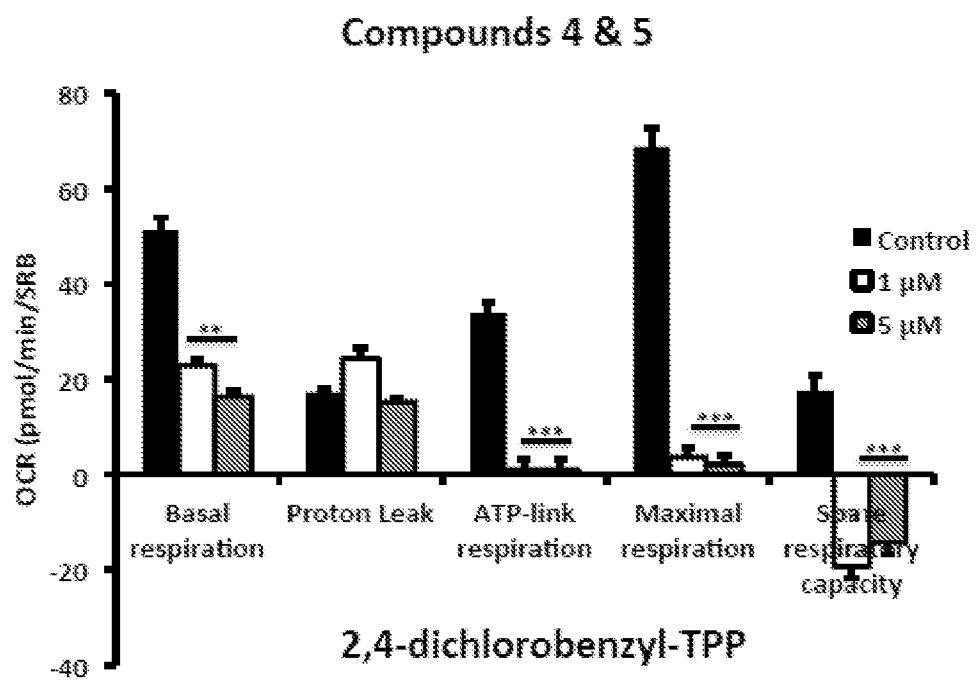
FIGS. 8A and 8B show impaired mitochondrial function of MCF-7 cells after treatment with TPP Compounds 4 (2,4-dichlorobenzyl-TPP) and 5 (1-napthylmethyl-TPP).
Figure 8B:
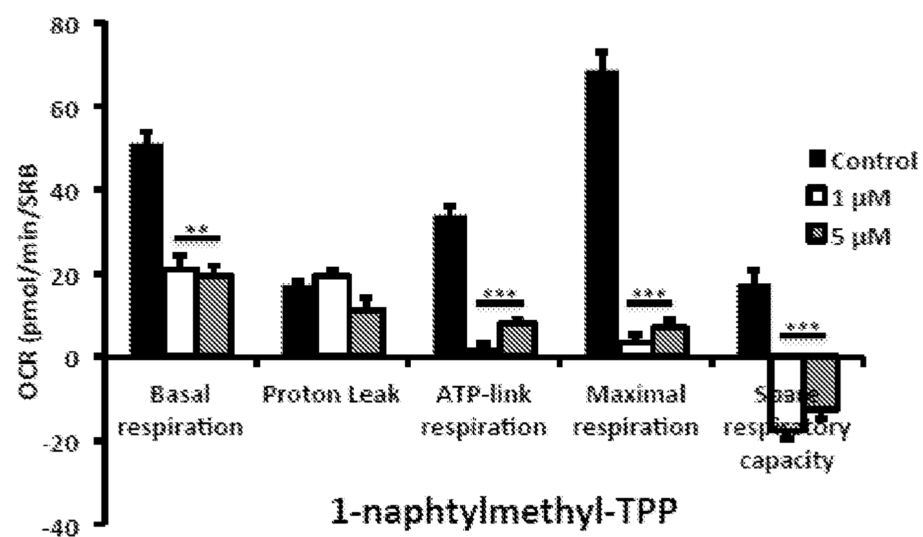

Some embodiments of the present approach relate to identifying TPP-derivatives compounds that target mitochondria in CSCs and represent potential anti-cancer therapies. To further validate that the ATP level reduction of the TPP compounds was indeed due to the inhibition of mitochondrial function, we directly measured mitochondrial oxygen consumption rates (OCR) using the Seahorse XFe96 metabolic flux analyser. The results are shown in FIGS. 6-8. All five TPP Compounds behaved similarly, and effectively reduced basal mitochondrial respiration, with an IC-50 of approximately 1 μM. The identified TPP-derivatives also showed significant reduction in ATP-link respiration, maximal respiration, and spare respiratory capacity.

FIG. 6 illustrates the impaired mitochondrial function of MCF-7 cells after treatment with TPP Compound 1. FIGS. 7A and 7B illustrate the impaired mitochondrial function of MCF-7 cells after treatment with either TPP Compound 2 or TPP Compound 3. FIG. 8 shows the impaired mitochondrial function of MCF-7 cells after treatment with either TPP Compound 4 or TPP Compound 5. Oxygen consumption rate (OCR) was measured with a Seahorse XF96 Extracellular Flux Analyzer. Data are represented as mean+/−SEM. Note that 2-butene-1,4-bis-TPP effectively inhibits mitochondrial oxygen consumption. For FIG. 6, $p<0.01$; *$p<0.001$; indicates significance, all relative to the control. Note that 2-chlorobenzyl-TPP and 3-methylbenzyl-TPP both effectively inhibit mitochondrial oxygen consumption. For FIG. 7, $p<0.01$; *$p<0.001$; indicates significance, all relative to the control. Note that 2,4-dichlorobenzyl-TPP and 1-naphtylmethyl-TPP both effectively inhibit mitochondrial oxygen consumption. And for FIG. 8, $p<0.01$; *$p<0.001$; indicates significance, all relative to the control.

Figure 9:
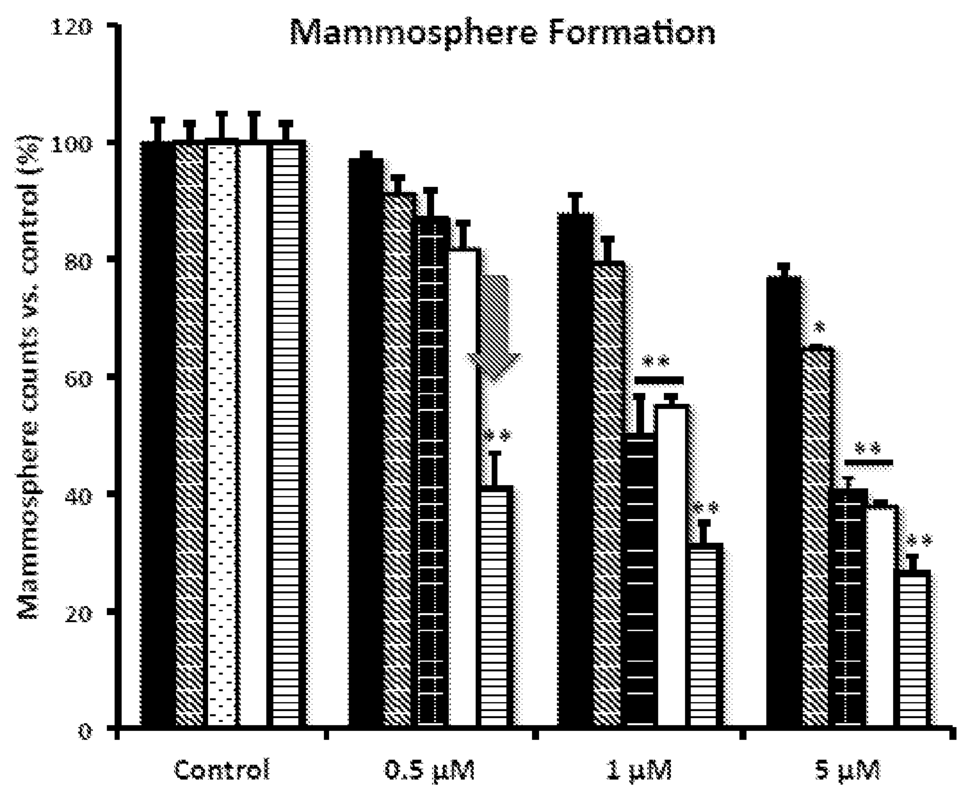
FIG. 9 illustrates the differential inhibition of the mammosphere-forming activity of MCF-7 breast CSCs, after treatment with TPP-derivatives.

Following validation, the inventors evaluated the effects of these TPP-derivative compounds on the propagation of CSCs, using the mammosphere assay as a read-out. FIG. 9 shows the differential inhibition of the mammosphere-forming activity of MCF-7 breast CSCs, after treatment with various TPP derivatives. The data presented in FIG. 9, from left to right, are TPP-derivatives in the following order: 2,4-dichlorobenzyl-TPP (black); 1-naphthylmethyl-TPP (inclined lines); 3-methylbenzyl-TPP (dotted lines); 2-chlorobenzyl-TPP (white); 2-butene-1,4-bis-TPP (horizontal lines). Cells were treated for 5 days in mammosphere media. Data are represented as mean+/−SEM. Note that 2-butene-1,4-bis-TPP was the most effective compound for blocking CSC propagation, with an IC-50 less than 500 nM. *$p<0.05$; **$p<0.01$; indicates significance, all relative to the control.

Interestingly, 2-butene-1,4-bis-TPP was the most effective, with an IC-50<500 nM. In contrast, for two of the other compounds tested (2-chlorobenzyl-TPP; 3-methylbenzyl-TPP) the IC-50 was between 1 to 5 μM. Finally, 1-naphthylmethyl-TPP was the least potent, with an IC-50>5 μM. Therefore, the inventors concluded that 2-butene-1,4-bis-TPP is 2- to 10-fold more potent than the other TPP compounds, for targeting CSC propagation. This is despite the fact that the identified TPP-derivatives had nearly identical behavior in reducing mitochondrial respiration and ATP production. Therefore, another intrinsic property of 2-butene-1,4-bis-TPP allows it to better target CSCs than the other TPP Compounds explored in the inventors' confirmatory work.

Figure 10:
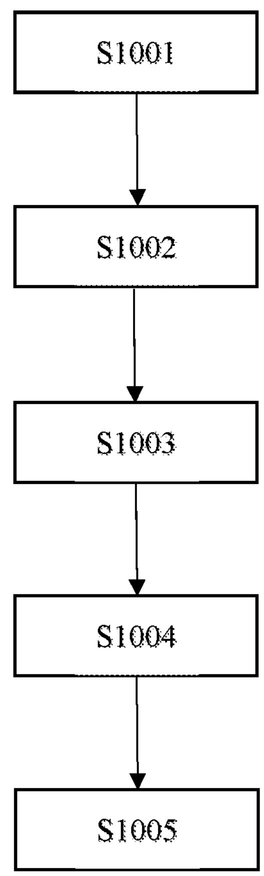
FIG. 10 shows a demonstrative approach for identifying mitochondrial inhibitors to target CSC propagation according to the present approach.

FIG. 10 shows an embodiment of the method according to the present approach: Identifying mitochondrial inhibitors to target CSC propagation. First, at S1001, prospective compounds are selected from a library and subjected to ATP-depletion assays in cancer cells. As discussed above, the inventors selected TPP-related compounds as the starting point for screening, because this ensures that all the compounds tested are targeted to mitochondria. It should be appreciated by those of ordinary skill in the art that other TPP-related compounds, or other compounds containing moieties having a demonstrated or expected capacity for targeting the mitochondrial membrane, may be selected under the present approach. Compounds that reduce ATP levels are then identified S1002, and then may be functionally validated S1003 through, as an example, an analysis mitochondrial oxygen consumption rates (OCR) such as discussed above. It should be appreciated that those having ordinary skill in the art may employ alternative assays to confirm that ATP level reduction of is due to the inhibition of mitochondrial function. Following validation, the effects of identified compounds on CSC proposition S1004 may be assessed. As discussed above, one embodiment of the present approach used mammosphere assays to assess CSC propagation effects, though those having ordinary skill in the art may use alternative approaches to assess the efficacy of an identified compound for targeting CSCs. The outcome of this approach is the identification of new compounds having CSC inhibition effects. Beneficially, as applied in the confirmatory analysis described herein, the present approach demonstrates that the identified TPP-derivatives are mitochondrial inhibitors of CSCs that are non-toxic in normal human fibroblasts, thereby effectively limiting drug toxicity.

FIG. 11 shows TPP-derivative referred to as bis-TPP. This TPP-derivative is an effective mitochondrial targeting signal for eradicating cancer stem cells (CSCs). The "dimeric" structure of bis-TPP is shown in the drawing, where R represents a chemical group or moiety. For example, R may be selected from the group consisting of hydrogen, carbon, nitrogen, sulfur, oxygen, fluorine, chlorine, bromine, iodine, carboxyl, alkanes, cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes, arene-based derivatives, heteroarene-based derivatives, phenols, phenol-based derivatives, benzoic acid, and benzoic acid-based derivatives.

Figure 12:
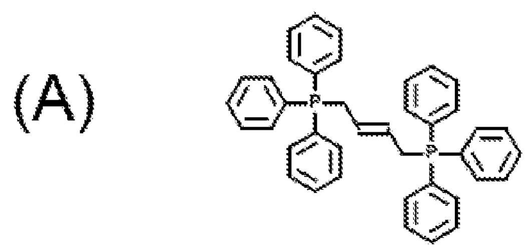
FIG. 12 shows structural activity relationships for selected TPP-derivatives (A) 2-butene-1,4-bis-TPP, and (B) p-xylene-bis-TPP.
Figure 12:
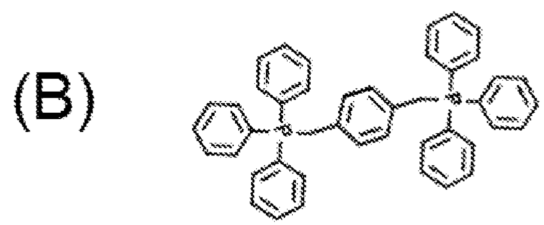

FIG. 12 shows the structural activity relationships of 2-butene-1,4-bis-TPP (see FIGS. 1 and 2) and p-xylylene-bis-TPP (see FIG. 1 and Table 1), the latter of which is approximately 200-fold less potent, in the context of ATP depletion. This demonstrates that while bis-TPP compounds may be effective for eradicating CSCs, some R groups may provide significantly more (or less) potency for targeting CSCs. Those having ordinary skill in the art will appreciate the need to evaluate each potential TPP-derivative compound's potency.

TABLE 1

Four Ineffective TPP Compounds.

| | Hoechst staining (%) | ATP level (%) |
|---|---|---|
| mito-TEMPO* | 100.0 | 100.0 |
| cyanomethyl-TPP | 97.2 | 95.1 |
| 4-cyanobenzyl-TPP | 72.7 | 68.2 |
| p-xylylenebis-TPP | 69.1 | 43.9 |

*(2-(2,2,6,6-tetramethylpiperidin-1-oxyl-4-ylamino)-2-oxoethyl-TPP Cell viability and intracellular ATP levels were determined in the same treated samples. MCF-7 cell line, 50 μM treatment for 72 hours.

The following paragraphs describe the materials and methods used in connection with the prior discussion. It should be appreciated that those having at least an ordinary level of skill in the art will be familiar with these methods.

With respect to cell culture and reagents, the human breast adenocarcinoma cell line (MCF-7) was from the American Type Culture Collection (ATCC). hTERT-BJ1 cells were from Clontech, Inc. MCF-7 and hTERT-BJ1 cells were grown in DMEM supplemented with 10% fetal bovine serum, GlutaMAX and 1% penicillin-streptomycin and incubated at 37 C in a humidified 5% CO2 incubator. The medium was changed 2-3 times/week. The TPP derivatives were from Santa Cruz Biotechnology, Inc., and included: (1) 2-butene-1,4-bis-TPP; (2) 2-chlorobenzyl-TPP; (3) 3-methylbenzyl-TPP; (4) 2,4-dichlorobenzyl-TPP; (5) 1-naphthylmethyl-TPP; (6) mito-TEMPO; (7) cyanomethyl-TPP; (8) p-xylylene-bis-TPP; (9) 4-cyanobenzyl-TPP.

With respect to the ATP-depletion assay (with CellTiter-Glo & Hoechst 33342), MCF-7 cells were treated with different TPP derivatives for 72 hours in a black 96-well plate then wells were washed with PBS and were stained with Hoechst 33342 dye at a final concentration of 10 μg/ml. Fluorescence was read by a plate reader at 355 nm (excitation), 460 nm (emission). After washing with PBS CellTiterGlo luminescent assay (Promega) was performed according to the manufacturer's protocols to determine intracellular ATP levels in the Hoechst dye stained cells. Both the fluorescent and luminescent data were normalized to control levels and were shown as percentage for comparison.

For measuring the mitochondrial OCR, mitochondrial function was determined by using the XF Cell Mito Stress Test Kit (Seahorse Bioscience, MA, USA) with a Seahorse XFe96 Extracellular Flux Analyzer (Seahorse Bioscience, MA, USA). MCF-7 cells were seeded in a specialized 96-well tissue culture plate (XF96 microplate). The next day, the TPP derivatives were added and the plate was incubated for 72 hours. Before the experiment media was changed to XF base medium (including 1 mM pyruvate, 2 mM glutamine and 10 mM glucose), cells were incubated at 37° C. in a CO2-free atmosphere for one hour before measurement. After detection of basal OCR (an indicator for mitochondrial respiration) OCR responses were evaluated towards the application of oligomycin (1 μM), FCCP (600 nM), and the combination of antimycin (1 μM) and rotenone (1 μM). From these measurements various parameters of mitochondrial function were determined. To determine cell viability in the measured wells sulphorodamine (SRB) assay was performed. Oxygen consumption rate values were then normalized to the given SRB values.

For the 3D Spheroid (mammosphere) assay, a single cell suspension of MCF-7 cells was prepared using enzymatic (1×Trypsin-EDTA, Sigma Aldrich, #T3924) and manual disaggregation (25 gauge needle) to create a single cell suspension. Cells were plated at a density of 500 cells/cm2 in mammosphere medium (DMEM-F12 media including B27/20 ng/ml and EGF/PenStrep) in non-adherent conditions, in culture dishes coated with (2-hydroxyethylmethacrylate) (poly-HEMA, Sigma, #P3932). Different TPP derivatives were previously diluted in the mammosphere media before addition of cells. Plates were maintained in a humidified incubator at 37° C. at an atmospheric pressure in 5% (v/v) carbon dioxide/air. After 5 days of culture, spheres >50 μm were counted using an eyepiece graticule and mammosphere numbers were normalized to control treatments (cells treated with vehicle only).

The foregoing description demonstrates that TPP-related compounds represent a novel chemical strategy for effectively targeting "bulk" cancer cells and CSCs, while minimizing off-target side-effects in normal cells. In this context, bis-TPP represents a more potent and selective form of TPP compounds, especially for targeting CSCs. Part of this potency and selectivity may also come from the reactive double bond in the central butene moiety, as p-xylylene-bis-TPP (see Table 1 above) was ~200 times less effective than 2-butene-1,4-bis-TPP (as shown in FIG. 2), in reducing overall ATP levels. FIG. 12 shows a side-by-side comparison of these two structures.

It should be appreciated that under the present approach, a therapeutic agent having an anti-mitochondrial effect, even if a side-effect or otherwise off-target property, may be used in connection with a TPP-derivative as an anti-cancer therapeutic. For example, TPP-derivatives may be administered covalently bonded with one or more therapeutic agents. The therapeutic agent may be a known pharmaceutical, including, for example, an FDA-approved antibiotic or other drug that has anti-mitochondrial side-effects. The therapeutic agent may be a mitochondrial biogenesis inhibitor, such as doxycycline, a mitoriboscin (mitoribosome-targeted therapeutics having anti-cancer and antibiotic properties), a mitoketoscin (non-carcinogenic compounds that bind to at least one of ACAT1/2 and OXCT1/2 and inhibit mitochondrial ATP production), an antimitoscin (an antibiotic having intrinsic anti-mitochondrial properties that are chemically modified to target the antibiotics to mitochondria), as additional examples. International Patent Application PCT/US2018/022403, filed Mar. 14, 2018, International Patent Application PCT/US2018/033466, filed May 18, 2018, and International Patent Application PCT/US2018/039354, filed Sep. 26, 2018, are each incorporated by reference in its entirety.

With respect to a mitoriboscin as a therapeutic agent, the agent may be a mitoribocycline, a mitoribomycin, a mitoribosporin, and/or a mitoribofloxin. The following compounds (or pharmaceutically acceptable salts thereof) are examples of agents that may be used:

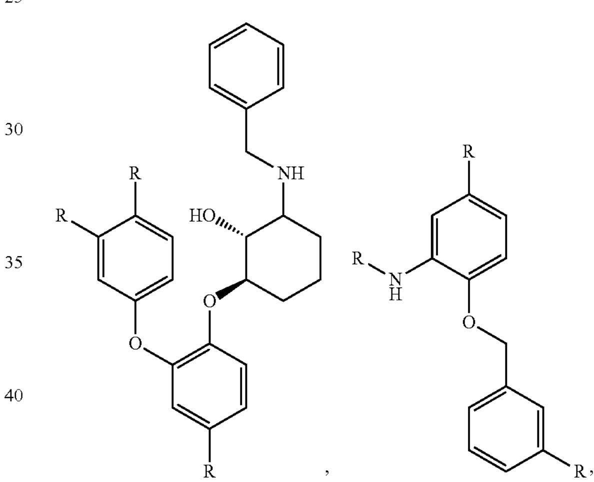

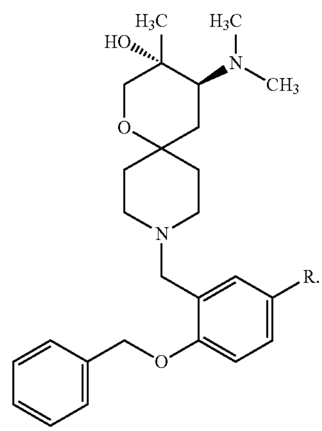

-continued

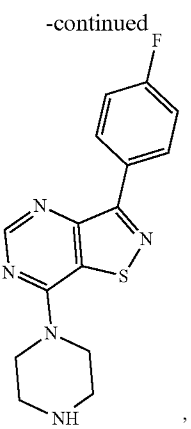

where each R may be the same or different and is selected from the group consisting of hydrogen, carbon, nitrogen, sulfur, oxygen, flourine, chlorine, bromine, iodine, carboxyl, alkanes, cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes, arene-based derivatives, heteroarene-based derivatives, phenols, phenol-based derivatives, benzoic acid, benzoic acid-based derivatives, and one or more mitochondrial targeting signals. For clarification, mitochondrial targeting signals are defined as any chemical or peptide entity that increases the efficiency of targeting the attached molecule to the mitochondria. Such modification would be expected to increase the potency and effectiveness of a mitoriboscin. Thus, R may be any mitochondrial targeting signal (peptide or chemical), including cationic compounds, such as tri-phenyl-phosphonium (TPP), a guanidinium-based moiety and/or choline esters, among others.

The therapeutic agent may comprise one or more of either or both an oxidative metabolism inhibitor and a glycolytic metabolism inhibitor. For example, an oxidative metabolism inhibitor may be a members of the tetracycline family and the erythromycin family. Members of the tetracycline family include tetracycline, doxycycline, tigecycline, minocycline, chlortetracycline, oxytetracycline, demeclocycline, lymecycline, meclocycline, methacycline, rolitetracycline, chlortetracycline, omadacycline, and sarecycline. Members of the erythromycin family include erythromycin, azithromycin, and clarithromycin. Inhibitors of glycolytic metabolism may be selected from inhibitors of glycolysis, inhibitors of OXPHOS, and inhibitors of autophagy. Inhibitors of glycolysis include 2-deoxy-glucose, ascorbic acid, and stiripentol. Inhibitors of OXPHOS include atoravaquone, irinotecan, sorafenib, niclosamide, and berberine chloride. Inhibitors of autophagy include chloroquine.

It should be appreciated that one or more TPP-derivatives may be the active ingredient in a pharmaceutical composition. For example, the TPP-derivative may be 2-butene-1,4-bis-TPP; derivatives of 2-butene-1,4-bis-TPP; 2-chlorobenzyl-TPP; derivatives of 2-chlorobenzyl-TPP; 3-methylbenzyl-TPP; derivatives of 3-methylbenzyl-TPP; 2,4-dichlorobenzyl-TPP; derivatives of 2,4-dichlorobenzyl-TPP; 1-naphthylmethyl-TPP; derivatives of 1-naphthylmethyl-TPP; p-xylylenebis-TPP; and derivatives of p-xylylenebis-TPP. Those of ordinary skill in the art will appreciate that a "derivative" of a TPP-derivative is a compound formed from the identified TPP-derivative, and may include structural analogs. The composition and/or the TPP-derivative compound may be in the form of a tablet, pill, powder, liquid, suspension, emulsion, granule, capsule, suppository, injection preparation, solution, suspension, and/or a topical cream. The pharmaceutical composition may include a therapeutic agent having an anti-mitochondrial effect. The therapeutic agent may be covalently bonded to the TPP-derivative.

In addition to bulk cancer cells and CSCs, it should be appreciated that TPP-derivative compounds may be used to target a hyper-proliferative cell sub-population that the inventors refer to as energetic cancer stem cells (e-CSCs). e-CSCs show progressive increases in sternness markers (ALDH activity and mammosphere-forming activity), highly elevated mitochondrial mass, and increased glycolytic and mitochondrial activity.

It should also be appreciated that TPP-derivative compounds may also have antibiotic and/or anti-senescence properties, among other valuable uses. For example, a TPP-derivative may be used for reducing or eliminating an age-associated illness such as atherosclerosis, cardiovascular disease, cancer, arthritis, cataracts, osteoporosis, type 2 diabetes, obesity, metabolic syndrome, hypertension, Alzheimer's disease, chronic inflammation, neuro-degeneration, muscle-wasting (sarcopenia), loss of skin elasticity, greying of the hair, male-pattern baldness, age spots, skin imperfections, and keratosis. TPP-derivatives may also be used for preventing senescence-associated secretory phenotype. In such embodiments, the TPP-derivative may be administered with a therapeutic agent having an anti-mitochondrial effect. The embodiment may take the form of a pharmaceutical composition having at least one TPP-derivative and at least on therapeutic agent having an anti-mitochondrial effect. The therapeutic agent may be covalently bonded to the TPP-derivative(s). In such embodiments, the TPP-derivative may be administered with a therapeutic agent having an anti-mitochondrial effect. The embodiment may take the form of a pharmaceutical composition having at least one TPP-derivative and at least on therapeutic agent having an anti-mitochondrial effect. The therapeutic agent may be covalently bonded to the TPP-derivative(s).

Depending on the therapeutic agent, methods and compositions as described herein may also have radiosensitizing activity, photosensitizing activity, and/or may sensitive cancer cells to one or more of chemotherapeutic agents, natural substances, and/or caloric restriction. Embodiments may also be useful for treating bacterial infection, pathogenic yeast infection, and aging. For example, the chemically modified therapeutic agent may also have enhanced anti-viral activity, enhanced anti-bacterial activity, and/or enhanced anti-microbial activity. Thus, embodiments of the present approach may also be used for targeting virus replication, preventing or reducing the growth of pathogenic bacteria, yeast, and parasites, overcoming drug resistance in bacteria (e.g., methicillin-resistant *Staph. Aureus*, or MSRA).

TPP-derivatives may also be used for reducing the effects of aging in an organism; treating at least one of atherosclerosis, cardiovascular disease, cancer, arthritis, cataracts, osteoporosis, type 2 diabetes, obesity, metabolic syndrome, hypertension, and Alzheimer's disease; increasing lifespan; promoting tissue repair and regeneration; and reducing aging-associated inflammation.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise. The invention includes numerous alternatives, modifications, and equivalents as will become apparent from consideration of the following detailed description.

It will be understood that although the terms "first," "second," "third," "a)," "b)," and "c)," etc. may be used herein to describe various elements of the invention should not be limited by these terms. These terms are only used to distinguish one element of the invention from another. Thus, a first element discussed below could be termed an element aspect, and similarly, a third without departing from the teachings of the present invention. Thus, the terms "first," "second," "third," "a)," "b)," and "c)," etc. are not intended to necessarily convey a sequence or other hierarchy to the associated elements but are used for identification purposes only. The sequence of operations (or steps) is not limited to the order presented in the claims.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

The term "about," as used herein when referring to a measurable value, such as, for example, an amount or concentration and the like, is meant to encompass variations of ±20%, ±10%, ±5%, ±1%, ±0.5%, or even ±0.1% of the specified amount. A range provided herein for a measurable value may include any other range and/or individual value therein.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

What is claimed is:

1. An anti-cancer pharmaceutical composition comprising at least one TPP-derivative compound comprising at least one of: 2-butene-1,4-bis-TPP; a derivative of 2-butene-1,4-bis-TPP; 2-chlorobenzyl-TPP; a derivative of 2-chlorobenzyl-TPP; 3-methylbenzyl-TPP; a derivative of 3-methylbenzyl-TPP; 2,4-dichlorobenzyl-TPP; a derivative of 2,4-dichlorobenzyl-TPP; 1-naphthylmethyl-TPP; a derivative of 1-naphthylmethyl-TPP; p-xylylenebis-TPP; and a derivative of p-xylylenebis-TPP.

2. The composition of claim 1, further comprising at least one therapeutic agent having an anti-mitochondrial effect.

3. The composition of claim 1, wherein the at least one TPP-derivative compound is 2-butene-1,4-bis-TPP.

4. The composition of claim 1, wherein the at least one TPP-derivative compound eradicates at least one of bulk cancer cells, cancer stem cells, energetic cancer stem cells, and normal senescent cells.

5. The composition of claim 1, wherein the TPP-derivative compound is non-toxic towards normal healthy cells.

6. The composition of claim 1, wherein the composition possesses at least one of radiosensitizing activity, photosensitizing activity, and activity to sensitive cancer cells to at least one of chemotherapeutic agents, natural substances, and caloric restriction.

7. A pharmaceutical composition comprising 2-butene-1,4-bis-TPP and at least one therapeutic agent having an anti-mitochondrial effect.

8. The pharmaceutical composition of claim 7, wherein the at least one therapeutic agent comprises at least one of an antibiotic, a mitochondrial biogenesis inhibitor, a mitoriboscin, a mitoketoscin, a mitoribocycline, a mitoribomycin, a mitoribosporin, a mitoribofloxin, an oxidative metabolism inhibitor, and a glycolytic metabolism inhibitor.

9. A method for treating at least one of tumor recurrence and metastasis, drug resistance, and radiotherapy resistance, the method comprising administering to a patient in need thereof a pharmaceutically effective amount of at least one TPP-derivative compound comprising at least one of: 2-butene-1,4-bis-TPP; a derivative of 2-butene-1,4-bis-TPP; 2-chlorobenzyl-TPP; a derivative of 2-chlorobenzyl-TPP; 3-methylbenzyl-TPP; a derivative of 3-methylbenzyl-TPP; 2,4-dichlorobenzyl-TPP; a derivative of 2,4-dichlorobenzyl-TPP; 1-naphthylmethyl-TPP; a derivative of 1-naphthylmethyl-TPP; p-xylylenebis-TPP; and a derivative of p-xylylenebis-TPP.

10. The method of claim 9, wherein the TPP-derivative compound comprises 2-butene-1,4-bis-TPP.

11. The method of claim 9, further comprising at least one therapeutic agent having an anti-mitochondrial effect.

12. The method of claim 11, wherein the at least one therapeutic agent having an anti-mitochondrial effect comprises at least one of an antibiotic, a chemotherapeutic, a nutraceutical, a mitochondrial biogenesis inhibitor, a mitoriboscin, a mitoketoscin, a mitoribocycline, a mitoribomycin, a mitoribosporin, a mitoribofloxin, an oxidative metabolism inhibitor, and a glycolytic metabolism inhibitor.

13. A method for preventing at least one of tumor recurrence and metastasis, drug resistance, and radiotherapy resistance, the method comprising administering to a patient in need thereof a pharmaceutically effective amount of at least one TPP-derivative compound comprising at least one of: 2-butene-1,4-bis-TPP; a derivative of 2-butene-1,4-bis-TPP; 2-chlorobenzyl-TPP; a derivative of 2-chlorobenzyl-TPP; 3-methylbenzyl-TPP; a derivative of 3-methylbenzyl-TPP; 2,4-dichlorobenzyl-TPP; a derivative of 2,4-dichlorobenzyl-TPP; 1-naphthylmethyl-TPP; a derivative of 1-naphthylmethyl-TPP; p-xylylenebis-TPP; and a derivative of p-xylylenebis-TPP.

14. The method of claim 13, further comprising at least one therapeutic agent having an anti-mitochondrial effect.

15. The method of claim 14, wherein the at least one therapeutic agent having an anti-mitochondrial effect comprises at least one of an antibiotic, a chemotherapeutic, a nutraceutical, a mitochondrial biogenesis inhibitor, a mitoriboscin, a mitoketoscin, a mitoribocycline, a mitoribomycin, a mitoribosporin, a mitoribofloxin, an oxidative metabolism inhibitor, and a glycolytic metabolism inhibitor.

16. A method for treating cancer, the method comprising administering to a patient in need thereof a pharmaceutically effective amount of at least one TPP-derivative compound comprising at least one of: 2-butene-1,4-bis-TPP; a derivative of 2-butene-1,4-bis-TPP; 2-chlorobenzyl-TPP; a derivative of 2-chlorobenzyl-TPP; 3-methylbenzyl-TPP; a derivative of 3-methylbenzyl-TPP; 2,4-dichlorobenzyl-TPP; a derivative of 2,4-dichlorobenzyl-TPP; 1-naphthylmethyl-TPP; a derivative of 1-naphthylmethyl-TPP; p-xylylenebis-TPP; and a derivative of p-xylylenebis-TPP.

17. The method of claim 16, further comprising at least one therapeutic agent having an anti-mitochondrial effect.

18. The method of claim 16, wherein the at least one TPP-derivative compound comprises 2-butene-1,4-bis-TPP.

19. The method of claim 16, wherein the at least one TPP-derivative compound selectively targets at least one of bulk cancer cells, CSCs, and energetic cancer stem cells.

20. The method of claim 19, wherein the at least one TPP-derivative compound selectively targets normal senescent cells.

21. The method of claim 16, wherein the at least one TPP-derivative compound is non-toxic to normal healthy cells.

22. The method of claim 17, wherein the at least one therapeutic agent having an anti-mitochondrial effect comprises at least one of an antibiotic, a mitochondrial biogenesis inhibitor, a mitoriboscin, a mitoketoscin, a mitoribocycline, a mitoribomycin, a mitoribosporin, a mitoribofloxin, an oxidative metabolism inhibitor, and a glycolytic metabolism inhibitor.

23. The method of claim 22, wherein the glycolytic metabolism inhibitor comprises at least one of a glycolysis inhibitor, an OXPHOS inhibitor, and an autophagy inhibitor.

24. A method for targeting a therapeutic agent to a cancer stem cell mitochondria, the method comprising chemically modifying the therapeutic agent with at least one TPP-derivative compound comprising at least one of: 2-butene-1,4-bis-TPP; a derivative of 2-butene-1,4-bis-TPP; 2-chlorobenzyl-TPP; a derivative of 2-chlorobenzyl-TPP; 3-methylbenzyl-TPP; a derivative of 3-methylbenzyl-TPP; 2,4-dichlorobenzyl-TPP; a derivative of 2,4-dichlorobenzyl-TPP; 1-naphthylmethyl-TPP; a derivative of 1-naphthylmethyl-TPP; p-xylylenebis-TPP; and a derivative of p-xylylenebis-TPP.

25. The method of claim 24, wherein the therapeutic agent has an anti-mitochondrial effect.

26. The method of claim 24, wherein the therapeutic agent comprises at least one of an antibiotic, a mitochondrial biogenesis inhibitor, a mitoriboscin, a mitoketoscin, a mitoribocycline, a mitoribomycin, a mitoribosporin, a mitoribofloxin, an oxidative metabolism inhibitor, and a glycolytic metabolism inhibitor.

27. The method of claim 24, wherein the chemically modified therapeutic agent comprises at least one of enhanced anti-viral activity, enhanced anti-bacterial activity, and enhanced anti-microbial activity.

* * * * *